United States Patent [19]
Franetzki

[11] Patent Number: 5,484,283
[45] Date of Patent: Jan. 16, 1996

[54] METHOD AND APPARATUS FOR TREATING HARD DENTAL SUBSTANCES

[75] Inventor: Manfred Franetzki, Bensheim, Germany

[73] Assignee: Siemens Aktiengesellschaft, Munich, Germany

[21] Appl. No.: 98,107

[22] Filed: Jul. 28, 1993

[30] Foreign Application Priority Data

Aug. 11, 1992 [DE] Germany ............... 42 26 612.2

[51] Int. Cl.⁶ ............... A61C 1/16; A61C 1/00; A61C 3/00
[52] U.S. Cl. ............... 433/116; 433/29; 433/215
[58] Field of Search ............... 433/215, 29, 30, 433/31, 116, 125, 126, 136, 137; 128/856, 857, 858, 859, 917, 918, 4, 6; 358/98, 229

[56] References Cited

U.S. PATENT DOCUMENTS

| | | | |
|---|---|---|---|
| 465,265 | 12/1891 | Hansen | 433/137 |
| 4,344,758 | 8/1982 | Wielhouwer et al. | 433/136 X |
| 4,522,196 | 6/1985 | Cunningham et al. | 128/4 |
| 4,561,427 | 12/1985 | Takada | 128/4 |
| 4,696,645 | 9/1987 | Saupe et al. | 128/66 |
| 4,727,416 | 2/1988 | Cooper et al. | 358/98 |
| 4,757,381 | 7/1988 | Cooper et al. | 358/98 |
| 4,810,194 | 3/1989 | Snedden | 433/116 |
| 4,858,001 | 8/1989 | Milbank et al. | 358/98 |
| 4,865,021 | 9/1989 | Siderman | 433/125 |
| 4,917,603 | 4/1990 | Haack | 433/29 |
| 4,969,473 | 11/1990 | Bothwell | 128/858 |
| 4,976,254 | 12/1990 | Dash et al. | 128/857 X |
| 4,991,564 | 2/1991 | Takahashi et al. | 128/4 |
| 5,016,098 | 5/1991 | Cooper et al. | 433/29 X |
| 5,049,070 | 9/1991 | Ademovic | 433/29 |
| 5,178,536 | 1/1993 | Werly et al. | 433/29 |

FOREIGN PATENT DOCUMENTS

| | | |
|---|---|---|
| 0280823 | 9/1988 | European Pat. Off. . |
| 9204412 | 7/1992 | Germany . |
| WO91/03209 | 3/1991 | WIPO . |

*Primary Examiner*—Nicholas D. Lucchesi
*Attorney, Agent, or Firm*—Hill, Steadman & Simpson

[57] ABSTRACT

A method and apparatus for treating hard dental substances wherein the work can be carried out in an indirect technique uses an intraoral video camera, whose images are reproduced on a monitor. To accomplish this and to prevent particles and bacteria in the patient's mouth from being spread, the apparatus includes a shielding which is arranged on the patient's mouth to prevent the emergence of particles but to allow the insertion of the treatment handpieces, the camera into the mouth and to the treatment location.

19 Claims, 5 Drawing Sheets

5,484,283

METHOD AND APPARATUS FOR TREATING HARD DENTAL SUBSTANCES

BACKGROUND OF THE INVENTION

The present invention is directed to a method and to an apparatus for treating hard dental substances with a treatment handpiece with which a cooling agent, such as air and/or water, can be supplied to the preparation location.

Treatment handpieces with which different preparations can be carried out at a tooth, such as, for example, treating a cavity, grinding a tooth or removing dental calculus, can be air-driven handpieces, electromotively-driven handpieces, ultrasound-driven handpieces or laser handpieces. In all of these preparation jobs, a coolant, for example cooling water or spray, is usually supplied to the preparation location. A disadvantage of such handpieces is that the supplied coolant forms an aerosol cloud with which bacteria are also entrained. Thus, the bacteria can be carried out of the patient's mouth and into the surroundings of the dental practice or office.

SUMMARY OF THE INVENTION

An object of the present invention is to provide a method and apparatus with which the aerosol cloud formed in the patient's mouth during a preparation and the particles contained therein can be prevented from emerging from the patient's mouth in an uncontrolled fashion without vision of the preparation location being greatly deteriorated.

The invention is based on the perception that a largely germ-free surrounding or at least a surrounding, that is low in germs with regard to bacterial contamination proceeding from the patient's mouth, can be created by a combination of an indirect preparation technique with a shielding to be attached to the patient's mouth given the assistance of an extraction device or suction device outside of the patient's mouth.

The inventive proposed method allows work with an indirect view under conditions that are especially hygienically favorable.

Particular advantages occur given a treatment method that has, again, become recently current. Such a treatment method utilizes an air stream laced with abrasive particles which is directed onto the preparation location at high speed instead of using a rotating or oscillating treatment tool. The erosion rate is therefore defined by the kinetic energy of the particles, the quantity of particles per unit of time, such as the mass stream, and the hardness and impact strength of the particles. The kinetic energy is defined by the density, the size and speed of the particles.

The effect on the substance to be treated, for instance coarse treatment of dental enamel, fine erosion of dentine in the proximity of the pulp or removal of dental plaque, can be optimized on the basis of the suitable selection of the above-mentioned parameters.

Since particles remaining in the mouth can be disturbing, the employment of self-dissolving abradants, for example salt particles, are advantageously used.

It is not only the aerosol cloud with bacteria potentially contained therein but, when the method mentioned above is utilized, the abrasion material occurring in the preparation can also be collected and disposed of in a suitable way with the present invention.

The shielding can be a cloth arranged to extend over the patient's mouth and advantageously secured to the patient's head. The hands holding the treatment tool is inserted into the mouth under this cloth. A suitable foil can also be provided instead of a cloth. The aerosol cloud retained by the cloth or, respectively, by the foil cannot penetrate toward the outside but, on the contrary, is extracted from the patient's mouth during preparation in the usual way by an appropriate extraction or suction means. Given application of the above-mentioned salt particles or, respectively, sandblasting method, the material occurring during the preparation falls onto a bib lying on the neck and chest of the patient and it can be easily disposed of with this bib after the treatment has been completed. The dust or respective spray cloud can be removed with an extraction tube or cannula introduced into the mouth, wherein a slight under-pressure or vacuum is provided in the patient's mouth at the same time.

Alternatively, the shielding can also be composed of a hose or tube of fabric or soft paper, wherein the hose opening is directly applied to the patient's face to surround the mouth by a fastening means including being taped, being tied or being clamped and the instruments can be introduced through the other end of the tube or hose. Expediently, at least the end at which the instruments are introduced is fashioned especially elastically so that the hose places itself around the hand and the instrument of the treating person with a good conformity.

A simple alternative for the shielding provides that an elastic "bandage" that tightly closes the patient mouth, similar to a coffer dam, can be stretched in front of the patient's mouth. The processing tools can be inserted through pre-punched slots or slits and the treatment can, thus, be carried out.

The prerequisite for an indirect treatment technique is an intraoral video camera having the appropriate illumination means, wherein the intraoral pick-up is reproduced on a monitor.

Video cameras are known per se and are disclosed, for example, in U.S. Pat. No. 4,727,416, whose disclosure is incorporated herein by reference thereto and which was the basis for European 280 823. Also, they are disclosed in U.S. Pat. No. 4,858,001, whose disclosure is also incorporated herein by reference thereto. Video cameras in combination with treatment handpieces with rotating tools are disclosed in U.S. Pat. No. 5,049,070, whose disclosure is incorporated herein by reference thereto, and in combination with handpieces with an output laser emission in German Gebrauchsmuster 92 04 412. None of the teachings of these references disclose the inventive proposed measures of the present invention.

A number of versions are conceivable in view of the fashioning and arrangement of the camera. Thus, the video camera, at least in the parts necessary for image acquisition, and a suitable illumination means can be fixed in the mouth, for example, at a tooth lying opposite. It can be coupled to the suction handpiece or it can be arranged integrated in the treatment handpiece. As warranted, a camera and a suction cannula can also be arranged integrated in such a treatment handpiece.

The optical window of the video camera and of the illumination means are advantageously protected against damage with a transparent cover that is expediently fashioned as a throw-away article and that can be easily changed.

The protection of the optics given application of the afore-mentioned particle jet method can occur by an applied grating whose apertures are smaller than the particles employed. Alternatively, the outer part of the window can also be composed of a material which is transparent and harder than the abrasive material employed. Given employment of a transparent, elastic foil, this can be advantageously fashioned so that at least the front part or treatment head that contains the optical part is covered. What is also conceivable and lies within the framework of the invention is that the entire treatment handpiece can be covered with a sheath that is withdrawn and disinfected after use or, respectively, is appropriately disposed of as a throw-away article.

A number of exemplary embodiments of the present invention are set forth in the following description of the preferred embodiments, the drawings and claims.

DESCRIPTION OF THE PREFERRED EMBODIMENTS

Figure 1:
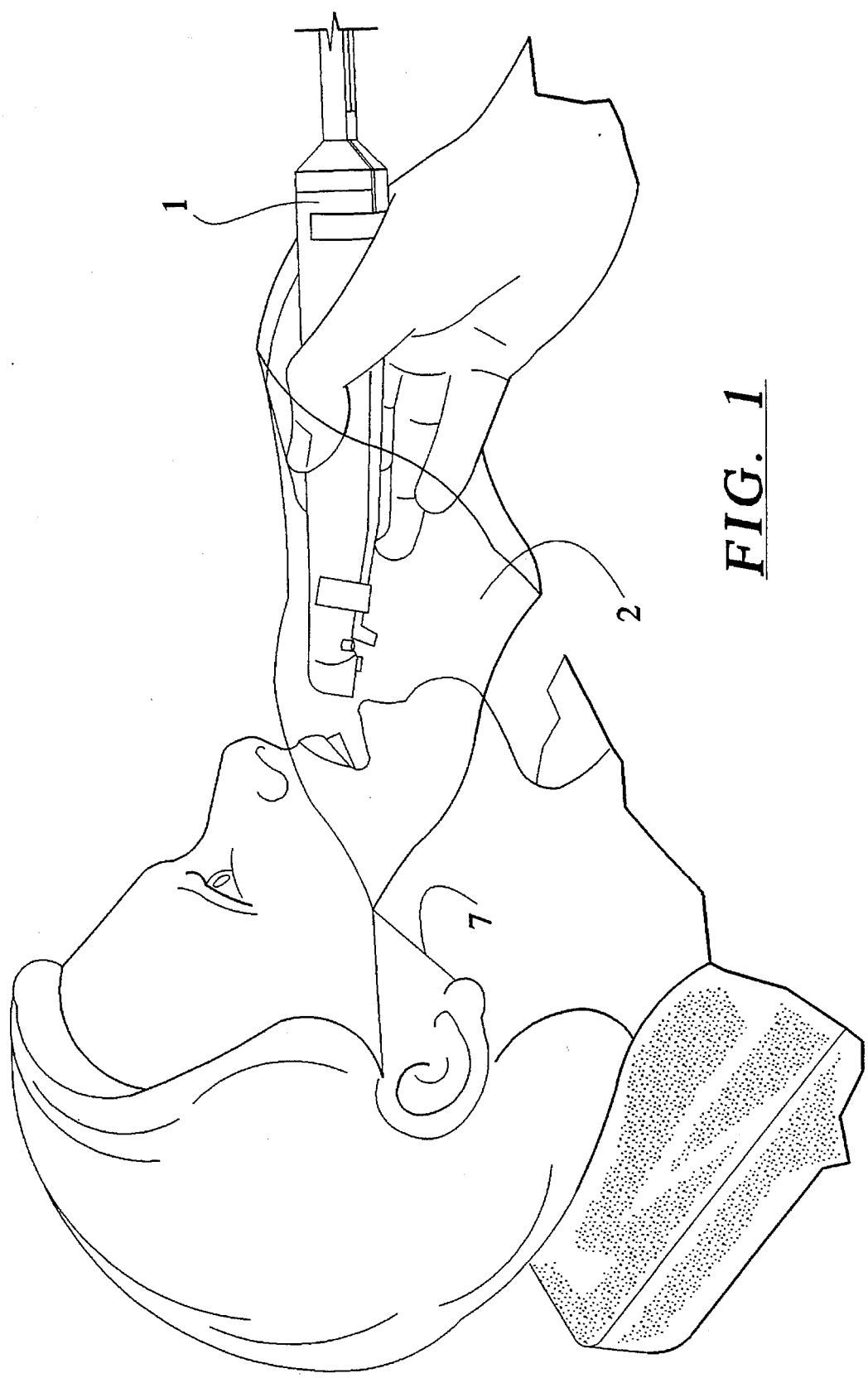
FIG. 1 is a perspective side view of a patient with a shielding in the form of a flexible hose or tube being treated in accordance with the present invention.

The principles of the present invention are particularly useful for treating a patient with a treatment handpiece 1 in FIG. 1. The treatment handpiece 1 is shown in greater detail in FIG. 4 and contains means for treating hard dental substances as well as means for illuminating the preparation field and an intraoral video camera whose image can be reproduced on a monitor, for example a monitor 4 in FIG. 3, which illustrates working in the indirect treatment technique.

In accordance with the present invention, one open end of a flexible hose or tube 2 is placed around the mouth of the patient and is secured on the face of the patient with suitable fastening means, such as 7, that extend around the ears of the patient. In addition, the end of the tube could be adhesively attached to the skin surrounding the mouth if desired. For treatment, the attending person reaches through the other opening or end of the hose or tube 2, as illustrated, to insert the treatment handpiece 1 into the patient's mouth. In this case, the handpiece contains an erosion tool, a video camera and illumination means.

Figure 3:
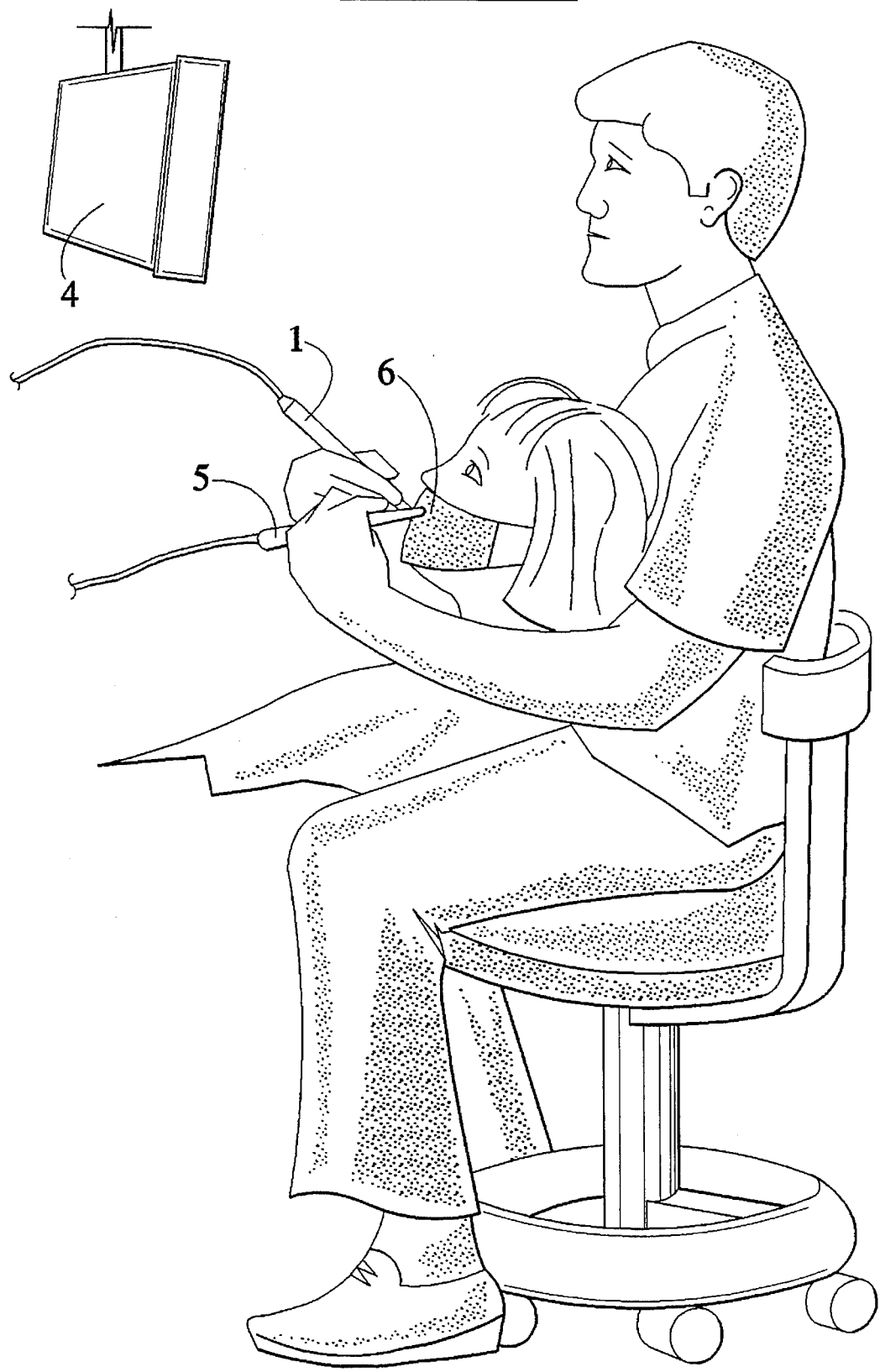
FIG. 3 is a perspective view of the patient having the shielding similar to FIG. 2 being treated in an indirect treatment from behind, wherein the treatment handpiece and video cameras are structurally separated from one another.

The preparation location can be treated in an indirect technique, wherein the operator utilizes a monitor 4 of FIG. 3. The aerosol cloud thereby occurs due to the supply of coolant or due to the treatment means, for example the abrasive salt or sand, as well as is extracted with a standard extraction cannula 5 that can be introduced into the patient's mouth in the same way. The hose 2, which can also be transparent, will provide optimum protection against the emergence of bacteria from the patient's mouth. Given application of salt or sand jet method, the abrasive particles that occur can be collected in the same way.

Figure 2:
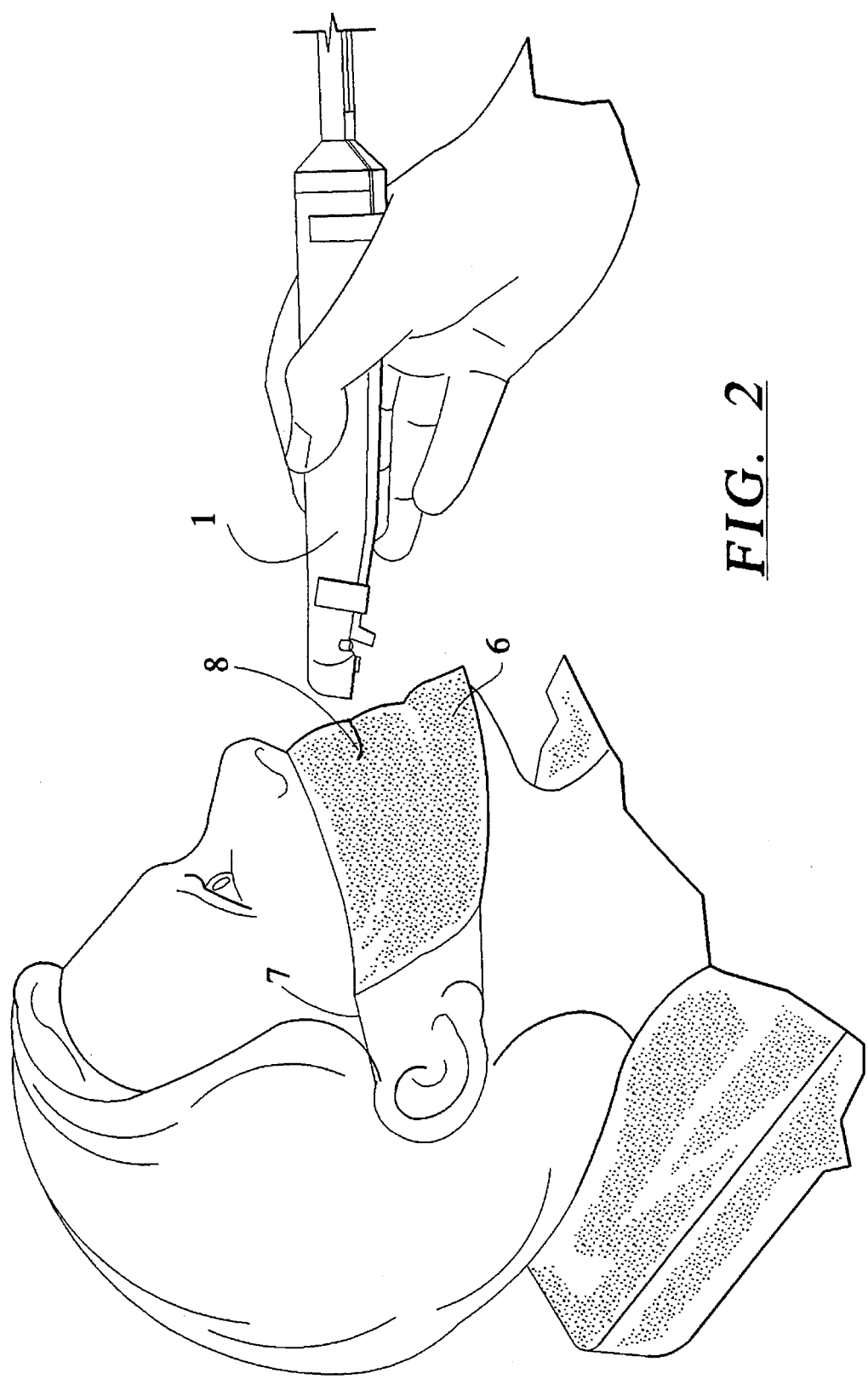
FIG. 2 is a perspective view of a patient with a second version of the shielding which comprises a stretched rubber member and illustrates treating from the front of the patient's mouth.

Instead of utilizing a hose or tube 2 as a shielding, an alternative is an elastic bandage 6 similar to a coffer dam which is stretched over the patient's mouth and is fixed to the patient's head by suitable fastening means 7, as illustrated in FIG. 2, which fastening means 7 extend around the patient's ear. The bandage or strip 6 contains one or more slots 8 in the region of the opening of the mouth and the treatment handpiece 1 is then inserted through the opening 8 into the patient's mouth.

In FIG. 3, a treatment in a 12 o'clock position with a monitor 4 that is aligned approximately in the 6 o'clock position is illustrated. The treatment handpiece 1 is self-sufficiently equipped with a coolant and light in a traditional way. The treatment handpiece can be a rotating instrument, a laser instrument, a sand jet instrument or some other type of instrument. The video camera may be combined with the suction cannula 5 and is separately introduced by the physician as shown or by an assistant. Both handpieces are plugged through the shielding foil or strip 6.

Figure 4:
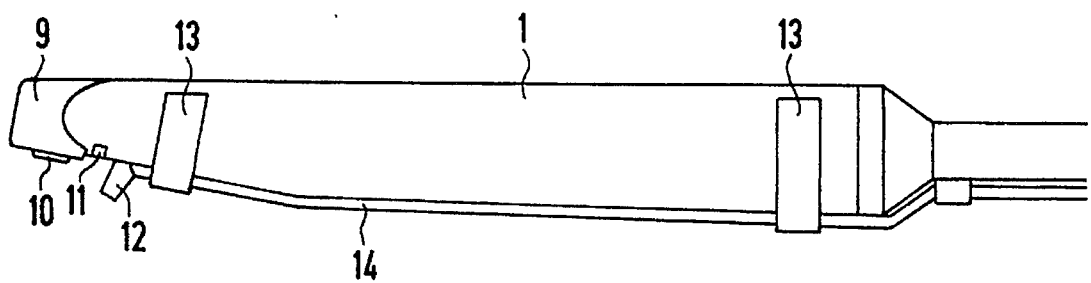
FIG. 4 is a side view of a treatment handpiece with an integrated video camera.

In FIG. 4, a treatment instrument 1 is fashioned in the manner of an angled handpiece. The pick-up optics for an intraoral video camera are arranged on the inside of the handpiece and are accommodated in the head housing 9. The structure of such a treatment handpiece with a video camera is disclosed, for example, in U.S. Pat. No. 5,049,070 or by U.S. Pat. No. 5,178,736, whose disclosure is incorporated herein by reference thereto and which corresponds to WO 91/03209. Since these structures are shown by existing U.S. Patents, a further detailed description is not included.

The head housing 9 at the face end is provided with an optical window 10 for the camera. A light exit end 11 is additionally provided so that illumination means can be provided or projected into the patient's mouth. A delivery pipe 14 is secured to the treatment handpiece 1 with suitable retaining means 13 and has an exit nozzle 12. Abrasive particles can be delivered with this delivery tube 14 with a high energy upon the addition of air and potentially water as a binding agent, and these particles exit through the nozzle 12.

Figure 5:
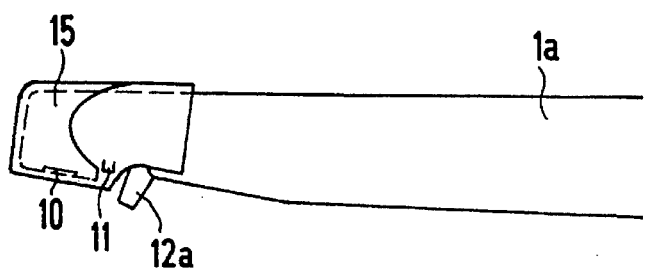
FIG. 5 is a partial side view of an embodiment of a treatment handpiece with an integrated video camera.

An embodiment of the handpiece 1a is shown in FIG. 5. In this embodiment, the delivery tube 14 is arranged integrated within the grasping member of the treatment handpiece 1a. The optical window 10 as well as the exit window 11 of the illumination means are protected here with a protective sheath 15 that can be placed onto the head housing. The sheath is transparent at least in the region of the exit windows 10 and 11 of the optics and protects the surface of the optics against damage, particularly due to abrasive particles emerging from the exit nozzle 12a. The sheath 15 can be a disposable or throw-away member.

Figure 6:
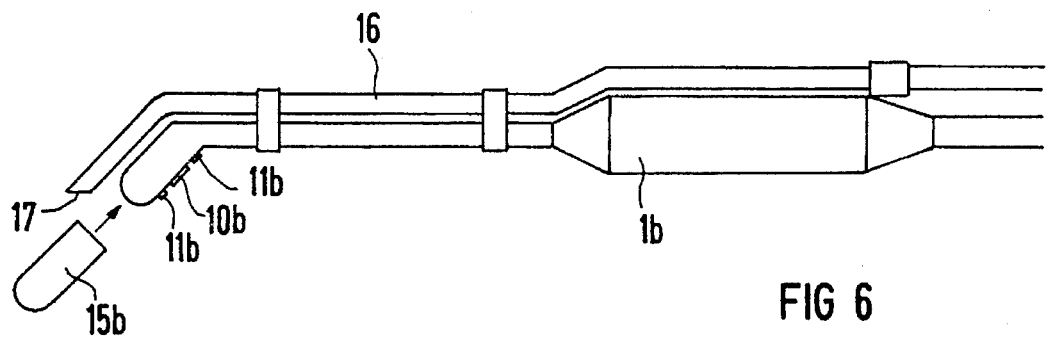
FIG. 6 is a side view of a treatment handpiece including a video camera combined with a suction cannula.

An intraoral camera handpiece 1b having an objective 10b and illumination openings 11b is illustrated in FIG. 6. A clip-on extraction cannula 16, which has an opening 17, is attached to the handpiece 1b. The optical parts of the handpiece can be protected by a transparent cover 15b that can be slipped on in the direction of the arrow.

Figure 7:
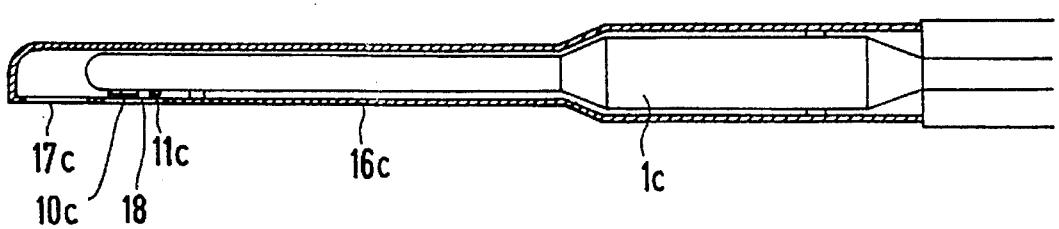
FIG. 7 is a partial cross sectional view with portions in elevation of another embodiment of a treatment handpiece including a video camera combined with a suction cannula.

In an embodiment of the extraction cannula is illustrated by a cannula 16c in FIG. 7 and the cannula is a sheath that passes over an intraoral camera handpiece 1c. The cannula can contain windows 18 for protection of the optical parts, such as the objective 10c and illumination exit 11c. The cannula 16c has an extraction opening 17c.

In order to avoid great pressure fluctuations in the mouth, it is expedient to adopt the extraction power or volume to the volume of spray or, respectively, sand jet stream. Means are thereby provided in the treatment location to regulate the extraction volume or suction so that either an equalized pressure or slight under-pressure or vacuum can be maintained within the patient's mouth.

Although various minor modifications may be suggested by those versed in the art, it should be understood that I wish to embody within the scope of the patent granted hereon all such modifications as reasonably and properly come within the scope of my contribution to the art.

I claim:

1. An apparatus for treating hard dental substances in an indirect treatment technique, said apparatus comprising in combination a treatment handpiece, extraction means, an intraoral video camera having a target subject reproducible on a monitor and shielding means, said shielding means adapted to be arranged at the patient's mouth to cover the mouth and to prevent the emergence of particles from the patient's mouth while enabling access to the entire interior of the mouth, said shielding means being a tube-shaped structure of flexibly deformable material that conforms to a body contour of the mouth and which allows insertion of a hand holding an instrument to enable the insertion and introduction of the treatment handpiece, the camera and the extraction means into the patient's mouth to a preparation location and still surround the handpiece, camera and extraction means to prevent the emergence of the particles.

2. An apparatus according to claim 1, wherein the shielding means is fashioned as a throw-away article.

3. An apparatus according to claim 1, wherein the treatment handpiece has a delivery tube extending to a nozzle with abrasive powder being carried in a flow of air and water to be discharged through the nozzle onto the treatment location.

4. An apparatus according to claim 3, wherein the nozzle and delivery tube are detachably secured to the treatment handpiece.

5. An apparatus according to claim 3, wherein the nozzle and delivery tube are integral components of the treatment handpiece.

6. An apparatus according to claim 1, wherein the camera is combined with an extraction cannula.

7. An apparatus according to claim 6, wherein the extraction cannula is clipped onto the camera.

8. An apparatus according to claim 6, wherein the extraction cannula is rigidly connected to the camera.

9. An apparatus according to claim 6, wherein the extraction cannula is a tube slipped over the camera as a sleeve so that it simultaneously serves as protection against damage to the optical parts of the camera.

10. An apparatus according to claim 1, wherein the video camera has an optical window and a window for illumination means arranged adjacent to the optical window, a cover of transparent material in the region of the windows being provided on said camera to provide protection for the windows.

11. An apparatus according to claim 10, wherein the cover is fashioned as a changeable disposable article.

12. An apparatus according to claim 1, wherein the treatment handpiece includes means for supplying an air/water stream and the apparatus includes an extraction line having a suction so that the pressure in the patient's mouth is either equalized or subjected to a slight suction.

13. A method of treating a hard dental substance in an indirect technique comprising covering a patient's mouth with shielding means comprising an elastic bandage with a slot to prevent the emergence of particles from the patient's mouth and to enable the insertion of a treatment handpiece into the patient's mouth and brought to a preparation location by stretching the bandage to conform to a body contour of the mouth and to deform to a shape of any instrument inserted into the slot to prevent the emergence of particles from the patient's mouth, said treatment handpiece acting in combination with an extraction means and an intraoral video camera, whose target subject is reproduced on a monitor, inserting the treatment handpiece with the intraoral video camera and the extraction means into the patient's mouth through the opening of the shielding means and observing the operation of the treatment handpiece on the monitor.

14. An apparatus for treating hard dental substances in an indirect treatment technique, said apparatus comprising in combination a treatment handpiece, extraction means, an intraoral video camera having a target subject reproducible on a monitor and shielding means, said shielding means being an elastic bandage with a slot adapted to be stretched over the patient's mouth to cover and close the mouth and to prevent the emergence of particles from the patient's mouth while enabling access to the entire interior of the mouth, said shielding means conforming to the body contour of the mouth and deforming to the shape of any instrument inserted into the slot to enable the insertion and introduction of the treatment handpiece, the camera and the extraction means into the patient's mouth to a preparation location and still surround and engage the handpiece, camera and extraction means to prevent the emergence of the particles.

15. An apparatus according to claim 14, wherein the shielding means is fashioned as a throw-away article.

16. An apparatus according to claim 14, wherein the treatment handpiece has a delivery tube extending to a nozzle with abrasive powder being carried in a flow of air and water to be discharged through the nozzle onto the treatment location.

17. An apparatus according to claim 14, wherein the treatment handpiece includes means for supplying an air/water stream and the apparatus includes an extraction line having a suction so that the pressure in the patient's mouth is either equalized or subjected to a slight suction.

18. An apparatus according to claim, 14, wherein the camera is combined with an extraction cannula.

19. An apparatus according to claim 14, wherein the video camera has an optical window and a window for illumination means arranged adjacent to the optical window, a cover of transparent material in the region of the windows being provided on said camera to provide protection for the windows.

* * * * *